United States Patent [19]

Berman et al.

[11] Patent Number: 4,784,149
[45] Date of Patent: Nov. 15, 1988

[54] INFRARED THERMOMETER WITH AUTOMATIC CALIBRATION

[75] Inventors: Herbert L. Berman, Los Altos Hills; Richard W. Singer, Palo Alto, both of Calif.

[73] Assignee: Optical Sensors, Inc., Los Altos, Calif.

[21] Appl. No.: 817,930

[22] Filed: Jan. 13, 1986

[51] Int. Cl.[4] ............................................. G01J 5/10
[52] U.S. Cl. .................................... 128/664; 128/736; 374/129; 374/158
[58] Field of Search ................ 128/664, 736; 374/129, 374/126, 158

[56] References Cited

U.S. PATENT DOCUMENTS

| | | | |
|---|---|---|---|
| 3,449,121 | 6/1969 | Astheimer | 73/355 R |
| 3,581,570 | 6/1971 | Wertz | 73/355 R |
| 3,673,868 | 7/1972 | Beury, III et al. | 73/343 R |
| 3,878,836 | 4/1975 | Twentier | 128/9 |
| 3,949,746 | 4/1976 | Twentier | 128/9 |
| 4,005,605 | 2/1977 | Michael | 374/129 |
| 4,343,185 | 8/1982 | Knute | 374/158 |
| 4,372,690 | 2/1983 | Berman et al. | 374/29 |
| 4,497,585 | 2/1985 | Paull et al. | 128/736 |
| 4,572,213 | 2/1986 | Kawahara | 128/736 |
| 4,602,642 | 7/1986 | O'Hara et al. | 128/664 |

Primary Examiner—Maryann Lastova
Attorney, Agent, or Firm—Flehr, Hohbach, Test, Albritton & Herbert

[57] ABSTRACT

Infrared radiation emitted from tissue surface of body cavity is measured by an infrared sensor located within a probe which generates a signal voltage dependent on the difference in temperature between the tissue and the infrared sensor. An additional ambient sensor measures the ambient temperature of the infrared sensor. The signals of the two sensors are added. To calibrate and eliminate errors, the housing of the device is provided with a chamber shaped to receive the probe and containing a target viewed by the infrared sensor. An error signal is thus generated which is added to the signals of the two sensors when they view the body tissue. A disposable, sanitary cover for the probe is made of a truncated polyethylene member of substantially uniform thickness closed by an end window. A filter in the probe suppresses absorption bands of polyethylene to eliminate errors due to minor variations in cover thickness.

13 Claims, 3 Drawing Sheets

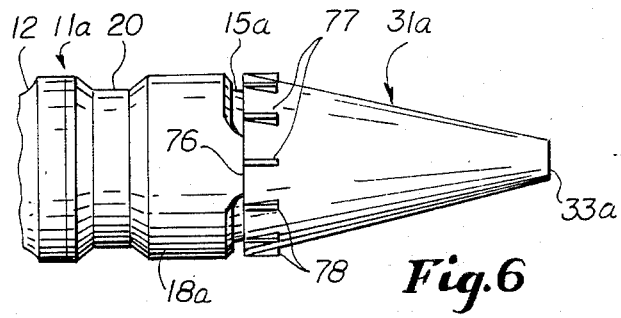
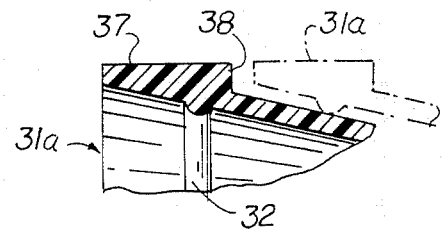
Fig. 6
Fig. 8
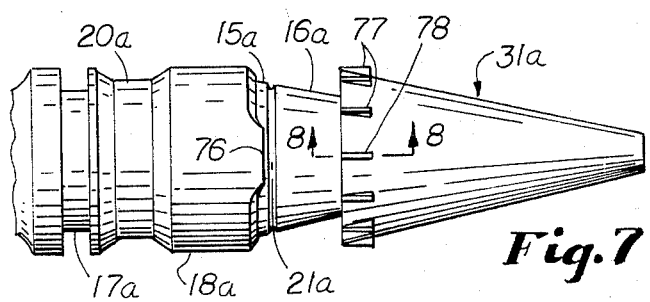
Fig. 7
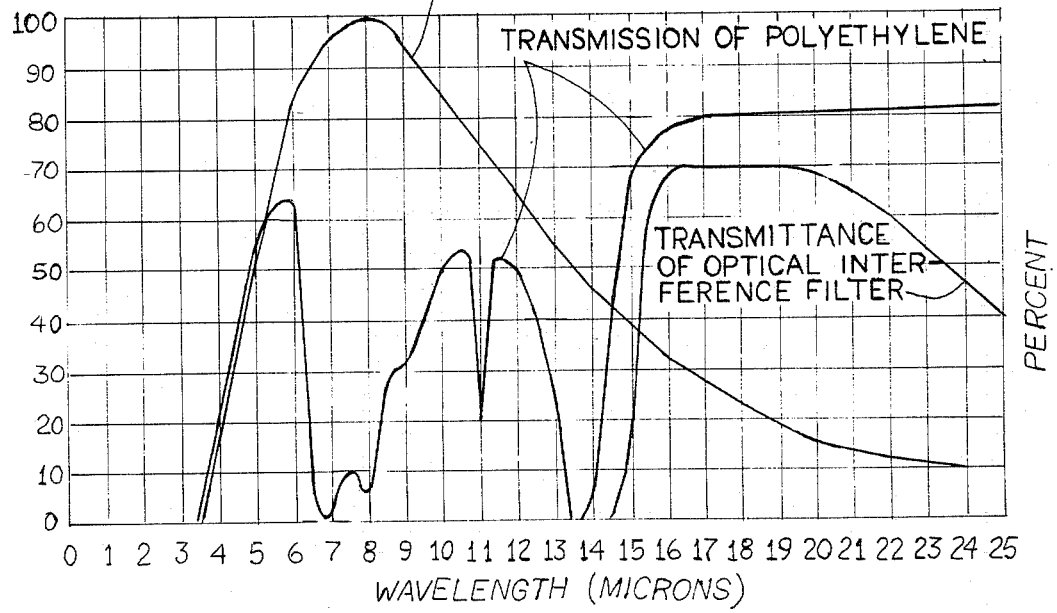
Fig. 5
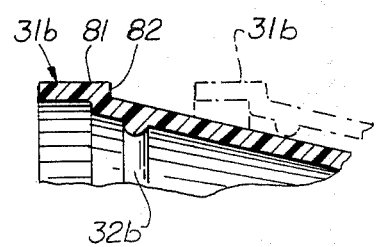
Fig. 9

4,784,149

INFRARED THERMOMETER WITH AUTOMATIC CALIBRATION

BACKGROUND OF THE INVENTION

1. Field of the Invention

This invention relates to a new and improved thermometer characterized by the fact that it measures infrared radiation emitted from body tissue.

2. Description of Related Art

Measuring body temperature by detecting infrared radiation from the tissue of body cavities is disclosed in U.S. Pat. No. 3,282,106. As hereinafter appears, the present apparatus is a considerable improvement over the structure and method disclosed in said patent.

Previous devices suffer from inaccuracies due to thermal artifacts and drift of IR and ambient sensors.

Various devices for measuring infrared radiation have been used and disclosed. However, the present invention provides a very accurate, specialized instrument useful in obtaining body temperatures of hospital and clinic patients, the details of which are not known to exist in the art so far as applicant is aware.

SUMMARY OF THE INVENTION

A hand-held probe has a truncated cone provided with a window to receive infrared radiation from the tissue surface of a body cavity (e.g. mouth). Within the probe is an infrared sensor which generates a signal voltage dependent on the difference in temperature between the tissue and the infrared sensor. An additional ambient sensor measures the ambient temperature of the infrared sensor. The signals of the two sensors are added.

To prevent contamination of the probe, the cone is covered by a disposable cover of polyethylene or other suitable material which may be affixed and detached without the nurse or physician touching the cover. To prevent minor variations in the thickness of the cover from affecting the reading, a filter in the probe suppresses the strong absorption bands of polyethylene. It has been found that at other weak absorbing wavelength regions, expected variations in the thickness of the polyethylene cover do not materially affect the reading of the sensor.

A casing is provided having a chamber into which the probe is inserted. At the end of the chamber is a target which is viewed by the infrared sensor. An error signal is created between the temperature sensed by the infrared sensor and the actual temperature of the target; and the error is added to the sum of the signals of the infrared and ambient sensors to provide a digital readout of the accurate temperature of the body cavity being measured.

Other objects of the present invention will become apparent upon reading the following specification and referring to the accompanying drawings in which similar characters of reference represent corresponding parts in each of the several views.

In the drawings:

FIG. 5 is a theoretical graph showing transmittance of different wavelengths of infrared radiation of polyethylene film and of an optical interference filter used in accordance with the present invention as well as the differential infrared emission from body tissue at 37° C. and ambient probe temperature.

FIG. 6 is a fragmentary side elevation of a modified probe and cover.

FIG. 7 is a view similar to FIG. 6 showing the slider in projected position.

FIG. 8 is an enlarged fragmentary sectional view of a modified cover.

FIG. 9 is a view similar to FIG. 8 of a further modified cover.

DESCRIPTION OF PREFERRED EMBODIMENT

Figure 1:
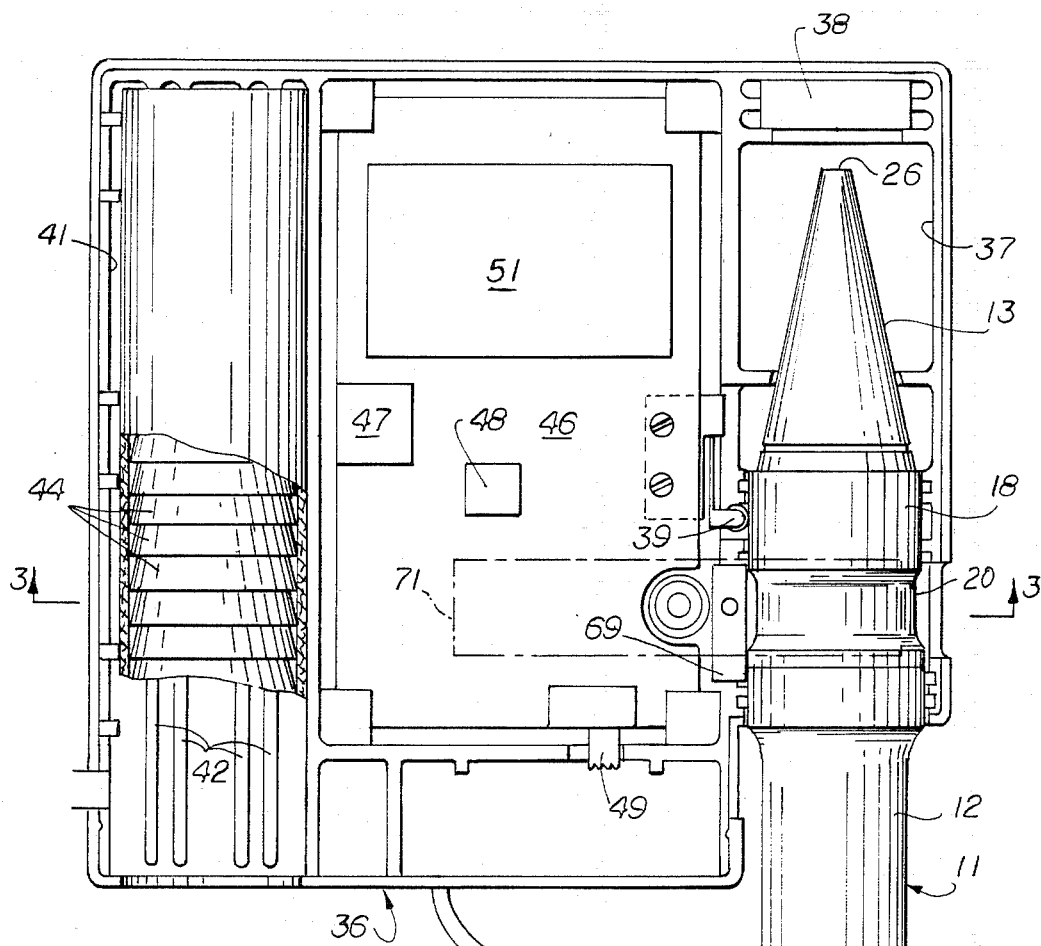
FIG. 1 is a plan view of the case of the present invention with parts removed and broken away to reveal internal construction.

The thermometer which is disclosed herein is designed to measure the temperature of a body cavity using infrared sensing techniques. Infrared radiation emitted by tissue surfaces collected by an infrared lens 24 and focused onto an infrared sensor 23. The infrared sensor 23 generates a signal voltage dependent on the temperature difference between the body tissue being observed and the infrared sensor.

To determine the true tissue temperature, an additional sensor 61 is used to measure the ambient temperature of the infrared sensor 23 and this ambient temperature is added to the signal voltage. The relationship between the signals to generate accurate tissue temperature is expressed $T_s = G(E_s - E_a) + T'_a$ Where $E_s$ is the radiant energy from the body tissue, $E_a$ is the radiant energy from the infrared sensor at ambient temperature and G is the gain of the infrared preamplifier.

The function $T'_a$ is generated from the measured infrared temperature $T_a$ and added to the infrared signal to produce an accurate value of body tissue temperature, $T_s$.

$T'_a$ compensates for the slight non-linearity in the signal $E_s - E_a$.

As used herein the ambient sensor 61 is a linear semiconductor device which generates a current proportional to its temperature. This sensor is attached to the infrared radiation sensor 23 for accurate tracking of the ambient temperature of the infrared sensor. The signal from the ambient sensor is added to that of the infrared sensor by means of the summing amplifier.

An important feature of the thermometer is the mechanism and associated circuitry for automatic calibration. This mechanism and circuitry eliminates or cancels measured temperature errors, which may result from temporal and thermal changes in the optical components and electronic circuitry. The calibration method utilizes an internal reference blackbody target 38, a comparator and an auto-zero circuit. At the initiation of the operation cycle, the "ON" switch is actuated while the probe 11 views the internal reference target 38. The signal generated by the probe is compared to the temperature of the reference target. If the probe measurement differs from the temperature of the reference target, an error signal is generated and "added" at the summing amplifier. Therefore, each time the probe is used, it is calibrated against a measured internal reference source.

Figure 2:
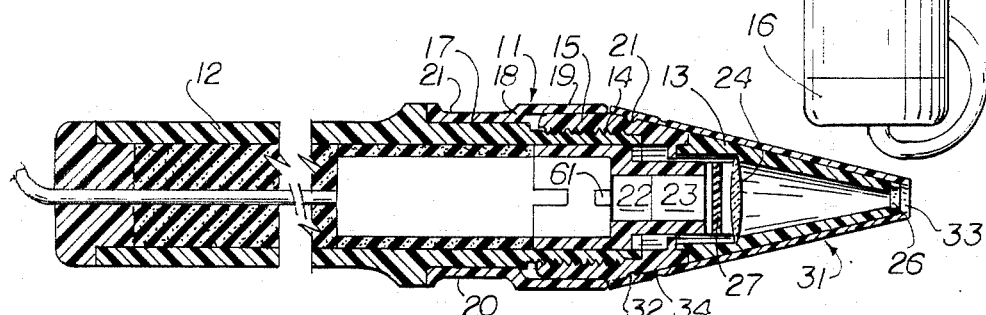
FIG. 2 is a fragmentary sectional view showing the protective cover in place on the cone of the probe.
Figure 2A:
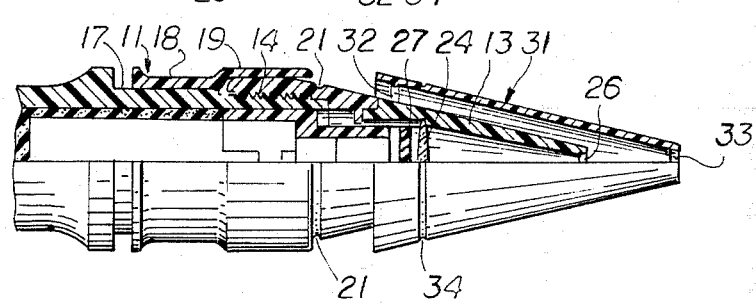
FIG. 2A is a view similar to FIG. 2 showing the slider in projected position to remove the cover from the cone.
Figure 3:
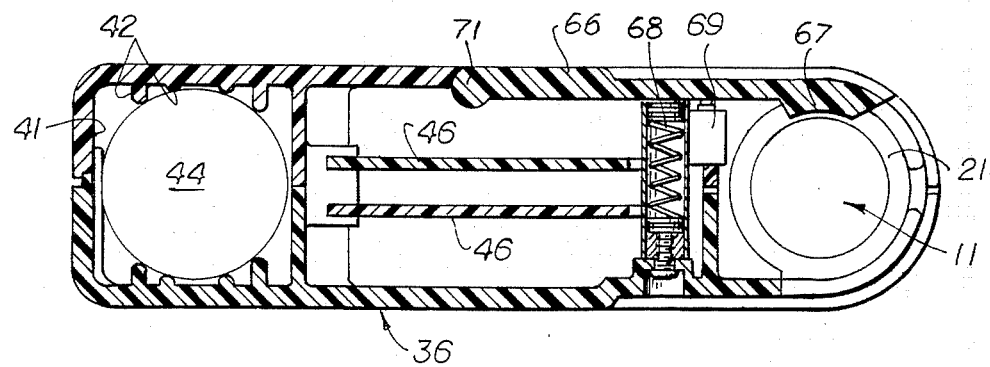
FIG. 3 is a sectional view taken substantially along line 3—3 of FIG. 1.

Directing attention now to FIGS. 1–3, probe 11 is formed with a body tube 12 containing certain electrical components not shown. A cone 13 is attached by means of fitting 15 to one end of tube 12 by threads 14. The opposite end of tube 12 may be closed by end cap 16. Adjacent the cone 13, the exterior of tube 12 is formed with a cylindrical slideway 17 around which fits a tubular slider 18 which is movable from the retracted position of FIG. 2 to the projected position of FIG. 2A by manual operation of the user. Slider 18 has a forward extension 19 which functions to remove the disposable cover 31 as hereinafter explained. An external groove 20 is formed in slider 18, also for a purpose hereinafter explained.

A circumferential groove 21 is formed in fitting 15 to engage the cover. Interiorly of probe 11 is a heat sink 22 to the distal face of which is attached an infrared sensor 23 and to sensor 23 is attached ambient sensor 61. Forwardly of sensor 23 is a converging lens 24 and between lens 24 and sensor 23 is a filter 27. At the distal end of cone 13 is a window 26 through which infrared radiation is received.

Cover 31 is formed in a conical shape of polyethylene or other suitable material. At its upper end is a circumferential internal protrusion 32 which snaps into the groove 21 and holds the cover 31 in close contact with the exterior cone 13. The distal end of cover 31 is formed with an end piece 33 the thickness of which is accurately controlled. However, as hereinafter explained, variations in thickness of end 33 are accommodated by filter 27. Endpiece 33 is recessed inward so that it does not contact body tissue and affect the accuracy of the temperature reading. On the exterior of cover 31, adjacent the proximal end thereof, is a circumferential receptor 34 into which protrusion 32 fits to improve nesting of the replacement covers 44.

Directing attention now to FIGS. 2 and 2A, with slider 18 in retracted position when the cone 13 is thrust into the cover 31, the protrusion 32 snaps into the groove 21, holding the cover 31 in place. In order to dislodge the cover 31 without touching it, the user pushes the slider 18 forwardly along the slideway 17 causing the extension 19 to engage the proximal end of the cover 31 and force it distally, causing the protrusion 32 to snap out of the groove 21, The cover 31 is then removed from the probe and may be disposed of in any convenient manner.

To achieve reasonable accuracy, the infrared transmission of the cover must be constant within reasonable limits. Expected variations in cover thickness should not result in appreciable changes in transmission. To minimize the effect of varying cover thicknesses (from part to part) a spectral filter 27 is employed to suppress those wavelength bands at which the cover absorbs the radiation.

Polyethylene is an appropriate cover material since it is readily molded and is relatively inexpensive. The spectral transmission of polyethylene film is shown in FIG. 5. At wavelengths beyond 15 microns, polyethylene exhibits high transmission and its transmission varies only slightly with thickness. To suppress the absorption bands of polyethylene, filter 27 is used which has the property of transmitting energy at wavelengths longer than 15 microns and reflecting energy at wavelengths shorter than 15 microns as is established from the graph of the transmittance of optical interference filter, FIG. 5. Thus, it will be seen that beyond 15 microns, the polyethylene film does not materially affect the reading of the sensor 23 despite minor variations in thickness of the film.

An alternative method of suppressing the absorption bands of the polyethylene cover is through the use of a thick section of polyethylene as a "filter". The thick material almost entirely absorbs in those spectral bands which exhibit high absorption coefficients, while transmitting in the non-absorbing regions.

In FIG. 1 is shown a case 36 which may be hand-held or strapped to the body of the user or placed on a table or bed. One side of case 36 has a chamber 37 having an inside dimension to receive the cone end of probe 11. At the back end of chamber 37 is a target 38 the function and characteristics of which have been explained. Switch 39 is placed on a wall of the chamber 37 so that when the probe 11 enters the chamber the switch is closed to energize the auto-calibration circuitry described above.

Storage of unused covers is provided on the opposite side of case 36. Thus, compartment 41 has internal ribs to engage and detachably retain removable tube 43 in which is shipped and stored a supply of replacement covers 44. The protrusion 32 of each cover 44 fits into the groove 34 of the next cover 44 to hold the nested covers 44 assembled. The probe 11 is inserted through the open end of tube 43 and the cone 13 fits inside the nearmost cover 44 until the protrusion 32 thereof snaps into the groove 21. The probe 11 is then withdrawn, carrying with it only one cover 44.

The central portion 46 of case 36 carries the electronic components of the system 47. There is also a manual "ON" switch 48 and another switch 49 which shifts the read-out of the display 51 from centigrade to fahrenheit as desired.

Figure 4:
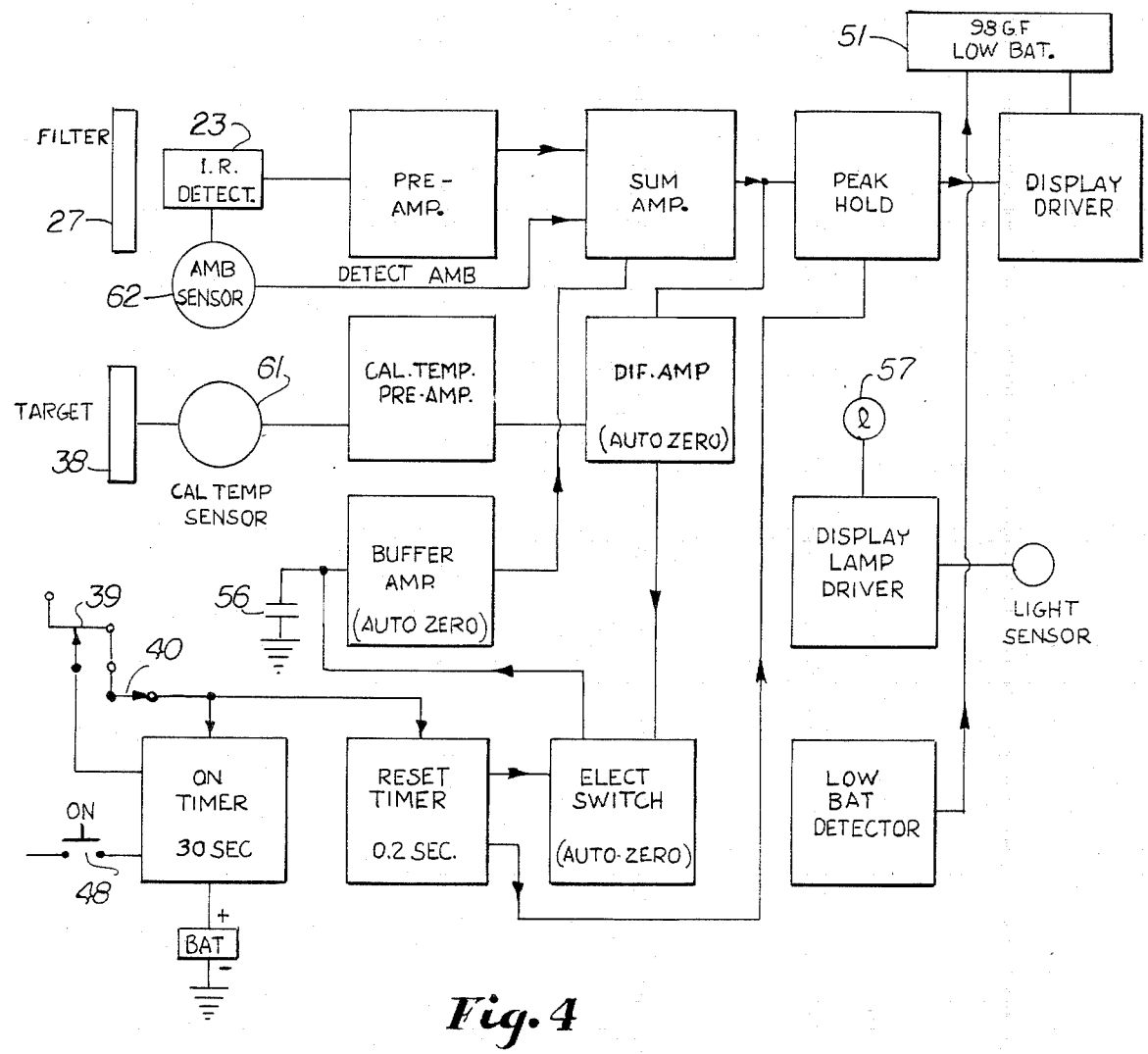
FIG. 4 is a schematic block diagram of the electrical circuitry.

Directing attention now to the block diagram FIG. 4, an automatic calibration circuit as a means to remove error signals in the infrared thermometer caused by infrared energy which reaches the detector and is not associated with the target temperature is provided. Such extraneous signals cause an offset in the output signal of the summing amplifier (SumAmp), the stage of an ordinary IR thermometer which adds the infrardd signal and the ambient signal and produces a voltage signal which can be displayed as temperature. Thus, it will be understood that ambient sensor 62 is in close thermal contact with the target 38. This produces a voltage signal which can be displayed as temperature by means of the electronic system set forth in FIG. 4. The circuitry shown in FIG. 4 eliminates the off set due to extraneous thermal signals and corrects the reading so that the signal is correct and true target temperature.

A small target 38 located in chamber 37 has an accurate temperature sensor 61 imbedded in it. The output of this sensor is amplified by the calibration temperature preamplifier (Cal.Temp.Pre-Amp.)

Located near target 38 is a switch 39 closed only when the probe is positioned in the chamber 37 and aimed at the target 38. Switch 39 must be closed to energize the circuitry and must also be closed to permit the function of the auto-calibration circuit.

To retain probe 11 within the chamber 37 for storage a strap 66 is hinged by hinge 71 at one end and has a detent 67 at the opposite end fitting into groove 20 when the probe 11 is fully inserted. Detent 67 is biased inwardly of chamber 37 by extension spring 68.

It is desirable that there be no cover 31 on cone 13 when the probe 11 is inserted in chamber 37. The pressure of such a cover forces strap 66 outward against the force of spring 68 and thereby opens switch 69 which is normally closed by spring 68.

On pressing the "ON" button 48, the "ON" timer is started for thirty seconds (e.g.) and the reset timer is operated for 0.2 seconds (e.g.). The "ON" timer turns on the unit and holds it on for thirty seconds, the reset timer has two functions, the first is to reset the peak-hold function and the second is to operate the automatic calibration circuit.

The output from the reset timer turns on the electronic switch (ElectSwitch) connecting the output of a difference amplifier (DifAmp) to the automatic zero storage capacitor 56. The buffer amplifier generates an off-set current which is input to the summing amplifier which forces its output to match the signal from the Calibration PreAmp. The electronic switch opens at the end of the reset time. The signal on the automatic calibration capacitor 56 remains and is not loaded by the very high input impedance of the buffer amplifier. The probe may now be moved away from the target 38 and pointed at the unknown temperature. The offset signal from the buffer amplifier will remain constant at intervals of thirty seconds. The correct temperature will then be read on the display 51.

At the end of the measurement interval, the unit will turn off automatically. The probe 11 must be re-aimed at the target 38, closing the probe switch 39 so that the unit can be turned on and the cycle repeated.

The peak-hold circuit is designed to display the highest observed temperature and hold that temperature reading so that the user can observe and record the reading which appears on the display 51.

If the battery voltage becomes low, the low battery detector causes a "Lo Batt" signal to be displayed.

Directing attention to FIGS. 6–8, a modified slider 18a is shown. Because of the possibility that removal of a cover 31a may be impeded by reason of friction or other factors if the slider pushes directly against the proximal end of the cover around the entire circumference thereof, the slider 18a has been modified to provide a finger 76 which contacts the back edge of the cover 31a in a localized area, rather than around the entire circumference. This results in a tilting of the cover 31a to the probe 11 and, hence, the resistance to removal is reduced. It will be understood that a finger 76 such as that shown in FIGS. 6 and 7 may be used in connection with the embodiment shown in FIGS. 1–4.

Directing attention to the covers 31a shown in FIGS. 6–8, to reduce the possibility that the nested covers in the compartment 41 may stick together so that withdrawing a single cover at a time becomes difficult, a plurality of fins 77 are formed on the outside of the cover 31a, the outer edge of the fins 77 being parallel to the longitudinal axis of the cover 31a and each fin 77 having a forward edge 78. The interior of the cover 31a is formed with an internal circumferential rounded protuberance 32a which fits into the groove 21 but also causes the covers to nest as shown in FIG. 8A, whereby the resistance to withdrawal of a single cover 31a at a time is reduced.

Directing attention to FIG. 9 a still further modified cover is shown in cross-section. In this modification, the rearward end 81 of the cover 31b is formed cylindrical. On the distal end of the cylindrical portion 81 is an inward directed flange 82 which merges with the conical body of the cover 31b. The internal protuberance 32b is formed in the conical portion of the cover 31b. The covers of FIG. 9 tend to nest in a manner so that they can be withdrawn from the compartment 41 one at a time.

It will be understood that the covers of FIGS. 6–8 and 9 may be used with the probe of FIGS. 1–4 or with other probe structures.

In other respects the modifications of FIGS. 6–8 and 9 resemble those of the preceding modification and the same reference numerals followed by the subscripts a and b, respectively, designate corresponding parts.

What is claimed is:

1. In combination, a probe for an infrared thermometer comprising a body, first means at one end of said body having a window at its distal end for admission of infrared radiation from tissue emitting radiation, an infrared sensor in said body emitting radiation, an infrared sensor in said body emitting a first signal responsive to the radiation entering through said window, said infrared sensor being in thermal equilibrium with said body to assume the temperature of said body, an ambient sensor in thermal contact with said infrared sensor emitting a second signal responsive to the temperature of said infrared sensor, second summing means summing the output signals of said sensors, third display means responsive to said summing means indicating the temperature of said tissue; and fourth means forming a chamber having an open first end and a closed second end, a target in said chamber adjacent said second end, said target being in thermal equilibrium with said fourth means to assume the temperature of said fourth means, whereby when said probe is inserted in said chamber it receives infrared energy of measured intensity from said target, and fifth error correcting means for adding an error signal to said second summing means to correct error in the signal from said infrared sensor.

2. A probe according to claim 1 which further comprises a removable disposable cover for said first means cone, said cover having an end positioned over said window, said end being of a material which transmits at certain wavelength bands and absorbs at other wavelength bands, and a filter in said body between said window and said infrared sensor which suppresses the absorption bands, whereby the signal of said infrared sensor is substantially insensitive to minor variations in thickness of said end.

3. A probe according to claim 2 in which said cover has a body and said end is recessed relative to said body.

4. A probe according to claim 2 in which one end of said body is conical and said cover is a thin-walled conical member, said one end being formed with a groove and the interior of said cover being formed with a protrusion fitting into said groove to hold said cover in place.

5. A probe according to claim 4 which further comprises a case, a container for replacement covers having an open end, means for detachably attaching said container to said case, and a plurality of replacement conical covers in said case nested inside each other with the largest end nearest said open end, whereby when a probe is inserted into said container, said probe engages the nearest replacement cover.

6. A probe according to claim 2 in which one end of said body is conical and said cover is a thin-walled conical member, the exterior of said cover being formed with shoulder forming means to provide shoulders spaced outward from the proximal end of said cover whereby said shoulders engage the proximal end of a second cover nested upon said first-mentioned cover, the interior of said first-mentioned cover being formed with a protrusion fitting into said groove to hold said cover in place.

7. A probe according to claim 6 in which said shoulder forming means comprises longitudinal fins.

8. A probe according to claim 6 in which said shoulder forming means comprises a short cylindrical section located proximally of said conical member, the diameter of said cylindrical section being greater than the external diameter of said conical member.

9. A probe according to claim 1 in which said error correcting means comprises a second sensor in thermal contact with said target.

10. A probe according to claim 1 in which said fourth means comprises a case and which further comprises a switch in said case positioned to be closed when said probe is inserted in said chamber, said switch, when closed, energizing said sensors and said target.

11. A probe according to claim 1 in which said fourth means comprises a case and which further comprises a switch positioned at the entrance to said chamber so as to be opened if a probe with the cover attached is inserted in said chamber, said switch, when opened, inactivating said probe.

12. A probe according to claim 1 which further comprises peak-hold means between said summing means and said display means to hold on said display means the highest temperature sensed by said probe.

13. A probe according to claim 10 which further comprises a timer energized upon closing of said switch to energize said sensors and said target only for a predetermined time.

* * * * *